(12) United States Patent
Nemoto

(10) Patent No.: US 8,211,067 B2
(45) Date of Patent: Jul. 3, 2012

(54) MECHANICAL SYSTEM

(75) Inventor: Shigeru Nemoto, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 1004 days.

(21) Appl. No.: 11/720,512

(22) PCT Filed: Nov. 29, 2005

(86) PCT No.: PCT/JP2005/021878
§ 371 (c)(1),
(2), (4) Date: May 30, 2007

(87) PCT Pub. No.: WO2006/059597
PCT Pub. Date: Jun. 8, 2006

(65) Prior Publication Data
US 2009/0131756 A1    May 21, 2009

(30) Foreign Application Priority Data

Nov. 30, 2004  (JP) .............................. 2004-345493

(51) Int. Cl.
| | |
|---|---|
| A61M 5/00 | (2006.01) |
| A61M 31/00 | (2006.01) |
| A61M 37/00 | (2006.01) |
| A61M 1/00 | (2006.01) |
| A61K 9/22 | (2006.01) |

(52) U.S. Cl. ............. 604/246; 604/65; 604/67; 604/131; 604/151; 604/890.1

(58) Field of Classification Search .................... 604/65, 604/110, 131, 151, 67, 890.1, 246; 600/300; 382/131; 340/540
See application file for complete search history.

(56) References Cited

U.S. PATENT DOCUMENTS

| 6,019,745 A * | 2/2000 | Gray .............................. 604/131 |
| 6,262,862 B1 * | 7/2001 | Kato et al. .................... 360/92.1 |
| 6,626,862 B1 * | 9/2003 | Duchon et al. ................ 604/110 |

(Continued)

FOREIGN PATENT DOCUMENTS

CN           1431918 A      7/2003

(Continued)

OTHER PUBLICATIONS

International Preliminary Report on Patentability for Application No. PCT/JP2005/021878, dated Jun. 14, 2007.

(Continued)

Primary Examiner — Kevin C Sirmons
Assistant Examiner — Bradley Thomas, Jr.
(74) Attorney, Agent, or Firm — Knobbe, Martens, Olson & Bear, LLP

(57) ABSTRACT

When consumable part such as pressure-resistant cover (300) is installed on a chemical solution injector (100), consumption degree data is read from storage means such as an RFID chip of the consumable part and temporarily held. If the consumption degree updated according to the use of the consumable part exceeds the consumption criteria, a replacement preliminary warning is outputted and the updated consumption degree data is written in the consumption storage means (310) of the consumable part. Since the consumption degree of a consumable part installed on a mechanical device is automatically detected and a replacement preliminary warning is issue to the user at an adequate timing, continuous use of a totally consumed part, unnecessary replacement of a non-totally consumed part is prevented.

9 Claims, 8 Drawing Sheets

U.S. PATENT DOCUMENTS 7,031,602 B2 * 4/2006 Faries et al. .................. 392/470

FOREIGN PATENT DOCUMENTS

| EP | 1272238 B1 | 8/2005 |
|---|---|---|
| JP | 04-323571 | 11/1992 |
| JP | 05-049647 | 3/1993 |
| JP | 10-283568 | 10/1998 |
| JP | 2000-293406 | 10/2000 |
| JP | 2002-101252 | 4/2002 |
| JP | 2002-200094 | 7/2002 |
| JP | 2002200094 * | 7/2002 |
| JP | 2003-215992 | 7/2003 |
| JP | 2003-290346 | 10/2003 |
| JP | 2004-121467 | 4/2004 |
| JP | 2004-281076 | 10/2004 |
| JP | 2004281076 * | 10/2004 |
| WO | WO 01/74421 | 10/2001 |
| WO | WO 01/88966 A2 | 11/2001 |
| WO | WO 03-011358 A2 | 2/2003 |

OTHER PUBLICATIONS

Chinese Office Action dated Mar. 30, 2010.

International Search Report from PCT/JP2005/021878 dated Jan. 17, 2006.

Office Action dated Jan. 24, 2011 in corresponding Japanese Application No. 2006-547939.

* cited by examiner

US 8,211,067 B2

MECHANICAL SYSTEM

CROSS REFERENCE TO RELATED APPLICATIONS

This application claims to benefit and priority to and is a U.S. National Phase of PCT International Application Number PCT/JP2005/21878, filed on Nov. 29, 2005, designating the United States of America, which claims priority under U.S.C. §119 to Japanese Application 2004-345493 filed on Nov. 30, 2004. The disclosures of the above-referenced applications are hereby incorporated by this reference in their entirety.

TECHNICAL FIELD

The present invention relates to a mechanism system in which a consumable part is removably mounted on a mechanical device and the consumable part is replaced when its durability is reduced to a predetermined level after the repeated use thereof, and more particularly, to a mechanical system including, as the consumable part, a cylinder adapter of a chemical solution syringe or a secondary battery.

BACKGROUND ART

Presently available imaging diagnostic apparatuses for capturing diagnostic images of patients include CT (Computed Tomography) scanners, MRI (Magnetic Resonance Imaging) apparatuses, PET (Positron Emission Tomography) apparatuses, ultrasonic diagnostic apparatuses, CT angiography apparatuses, MRA (MR angiography) apparatuses and the like. When the abovementioned imaging diagnostic apparatuses are used, a chemical solution such as a contrast medium or physiological saline may be injected into a patient. Chemical solution injectors for automatically performing the injection have been put into practical use.

Such a chemical solution injector has a piston driving mechanism formed of a driving motor, a slider mechanism and the like, for example. A chemical solution syringe is removably mounted on the injector. The chemical solution syringe typically includes a cylinder member and a piston member slidably inserted in the cylinder member. There are a pre-filled type and a refill type in the chemical solution syringe.

The chemical solution syringe of the pre-filled type includes a cylinder member filled with a chemical solution and is wholly sealed by a packing material for shipment. The chemical solution syringe of the refill type includes a cylinder member which can be filled with a desired chemical solution by a user. For simplicity, the following description will be made assuming that the chemical solution syringe of the pre-filled type is used.

When the chemical solution in the chemical solution syringe of the abovementioned type is injected into a patient, an operator prepares a chemical solution syringe containing an appropriate chemical solution and takes out the chemical solution syringe from the packing material. The operator connects the chemical solution syringe to a patient through an extension tube and mounts the chemical solution syringe on a chemical solution injector. The chemical solution injector moves the piston member relative to the cylinder member in response to predetermined operation to inject the chemical solution into the patient from the chemical solution syringe.

The operator determines the rate at which the chemical solution is injected and the total quantity of the chemical solution to be injected in view of the type of the chemical solution and the like, and enters data representing the rate and total quantity into the chemical solution injector. The chemical solution injector injects the chemical solution into the patient based on the entered data. For example, when a contrast medium is injected as the chemical solution, the image contrast of the patient is changed to allow the imaging diagnostic apparatus to capture a favorable diagnostic image of the patient.

The chemical solution injector for the abovementioned CT angiography apparatus injects a contrast medium with a high viscosity into a blood vessel, so that the piston member of the chemical solution syringe is pressed into the cylinder member at an extremely high pressure. The high pressure is likely to break the cylinder member if the chemical solution syringe is directly mounted on the chemical solution injector for use. To avoid this, in a mechanical system for the CT angiography apparatus, a cylinder adapter may be put on the cylinder member of the chemical solution syringe and used to hold the chemical solution syringe on the chemical solution injector (see, for example, non-patent document 1 below).

Non-patent document 1: "Angiography Contrast Medium Injector in product guides of Nemoto Kyorindo Co., Ltd" (retrieved in Jul. 14, 2004) (URL:http://www.nemoto-do.co.jp/seihin_ang.mr.html#120top)

In the chemical solution injector of the abovementioned type, since the cylinder member of the chemical solution syringe is held by the cylinder adapter, the piston member can be pressed into that cylinder member at a high pressure. The abovementioned cylinder adapter is formed of polycarbonate or polyamide 12 having a predetermined thickness or less since the interior of the chemical solution syringe needs to be visually checked when the cylinder adapter is used.

Thus, the abovementioned cylinder adapter cannot be formed as a permanently usable part but as a consumable part which needs replacement after a predetermined number of uses. However, it is difficult to control the number of uses of the cylinder adapter in a medical facility such as a hospital, and the cylinder adapter may be broken after it is used beyond the consumption limit. To prevent this, cylinder adapters are replaced once in a predetermined time period such as once in a year in some medical facilities, but in this case, a cylinder adapter which can still be used a number of times before the consumption limit may be replaced.

Some chemical solution injectors for the MRI apparatus employ a secondary battery as a power source. The secondary battery is also formed as a consumable part which requires replacement after a predetermined number of uses. However, it is also difficult to control the number of uses of the secondary battery in a medical facility such as a hospital, resulting in replacement of a secondary battery after it is used beyond the consumption limit or a secondary battery which can still be used a number of times before the consumption limit.

DISCLOSURE OF THE INVENTION

The present invention has been made in view of the above mentioned problems, and it is an object thereof to provide a mechanism system in which a consumable part can be replaced at the appropriate time.

The mechanical system according to the present invention includes a consumable part and a mechanical apparatus. The consumable part is replaced when its durability is reduced to a predetermined level after the repeated use thereof, and is removably mounted on the mechanical device. For example, the consumable part is realized by a chemical solution syringe, a cylinder adapter, a secondary battery or the like, and the mechanical apparatus is realized by a chemical solution injector, a battery-charging apparatus or the like. The consumable part has a consumption storage means put thereon for storing at least data of its consumption degree such that the data can be updated. The mechanical apparatus includes a part using means, a data reading means, a consumption holding means, a consumption detecting means, a consumption determining means, an alarm notifying means, and a data writing means.

The part using means of the mechanical apparatus uses and operates the consumable part removably mounted thereon. The data reading means reads the data of the consumption degree from the consumption storage means on the consumable part mounted thereon. The consumption holding means temporarily holds the read data of the consumption degree. The consumption detecting means updates the temporarily hold data of the consumption degree in accordance with the operation of the part using means. The consumption determining means determines whether or not the temporarily held consumption degree exceeds a predetermined consumption reference. The alarm notifying means outputs and notifies a predetermined replacement announcement when it is determined that the consumption degree exceeds the consumption reference. The data writing means writes the updated data of the consumption degree to the consumption storage means on the chemical solution syringe. Thus, the consumption degree of the consumable part mounted on the mechanical apparatus is automatically detected and a user is notified of the replacement announcement at the appropriate time.

Various means referred to in the present invention may be arranged to perform their functions, and may comprise dedicated hardware for performing a predetermined function, a data processing apparatus whose predetermined function is given by a computer program, a predetermined function performed in a data processing apparatus according to a computer program, or a combination thereof.

Various components referred to in the present invention do not need to be a separate entity. A plurality of components may be constructed as one member, a certain component may be part of another component, or a certain component may have a portion overlapping a portion of another component.

EFFECT OF THE INVENTION

In the mechanical system of the present invention, when the consumable part such as the chemical solution syringe, the cylinder adapter, and the secondary battery is mounted on the mechanical apparatus such as the chemical solution injector and the battery-charging apparatus, the data of the consumption degree is read out from the consumption storage means on the consumable part, and it is temporarily held by the mechanical apparatus. The data of the consumption degree is updated in accordance with the use of the consumable part, and if the consumption degree exceeds the consumption reference, the replacement announcement is output and notified to write the data of the consumption degree to the consumption storage means on the consumable part. As a result, the consumption degree of the consumable part mounted on the mechanical apparatus is automatically detected, and the user is notified of the replacement announcement at the appropriate time. This can prevent the continued use of the consumable part which has been used up or unnecessary replacement of the consumable part which has not been used up. Particularly, the consumable part itself manages the data of the consumable degree. When a plurality of consumable parts are simultaneously used, each consumption degree of the parts can be automatically managed without requiring complicated operation.

DESCRIPTION OF REFERENCE NUMERALS

100 CHEMICAL SOLUTION INJECTOR
117 PISTON DRIVING MECHANISM SERVING AS PART USING MEANS
120 RFID READER/WRITER SERVING AS DATA READING MEANS AND DATA WRITING MEANS
143 CONSUMPTION HOLDING MEANS
144 CONSUMPTION DETECTING MEANS
145 CONSUMPTION DETERMINING MEANS
146 ALARM NOTIFYING MEANS
200 CHEMICAL SOLUTION SYRINGE
210 CYLINDER MEMBER
220 PISTON MEMBER
300 PRESSURE-RESISTANT COVER WHICH IS CONSUMABLE PART
310 RFID CHIP SERVING AS CONSUMPTION STORAGE MEANS
1000 IMAGING DIAGNOSTIC SYSTEM SERVING AS MECHANICAL SYSTEM

BEST MODE FOR CARRYING OUT THE INVENTION

[Configuration of Embodiment]
An embodiment of the present invention will hereinafter be described with reference to FIGS. 1 to 8. As shown in FIGS. 1 to 4, imaging diagnostic system 1000 serving as a mechanical system of the embodiment according to the present invention includes a chemical solution injector 100, a chemical solution syringe 200, a CT angiography apparatus 400 serving as an imaging diagnostic apparatus, and a pressure-resistant cover 300 serving as a cylinder adapter, and injects a contrast medium or the like as a chemical solution into a patient (not shown), although described later in detail.

Figure 3:
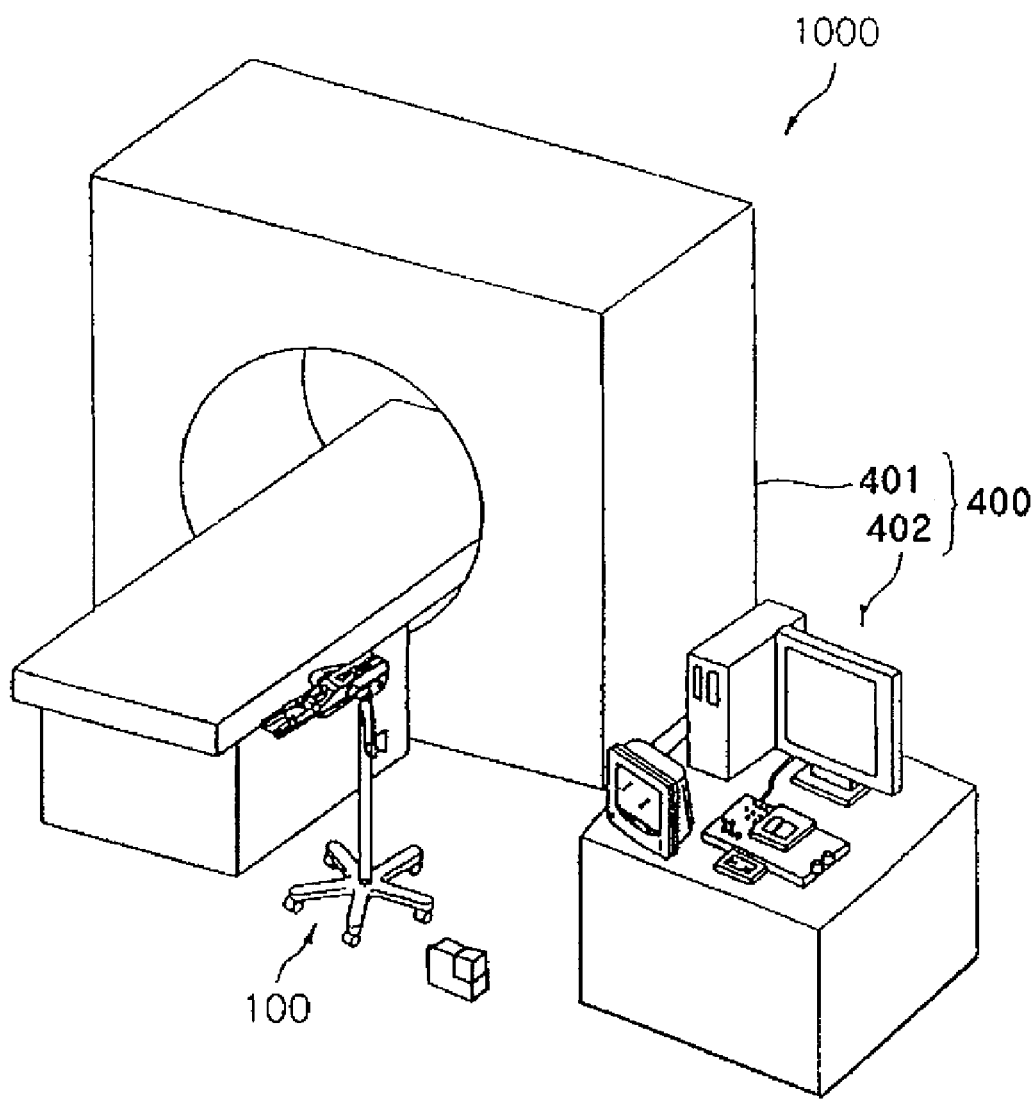
FIG. 3 is a perspective view showing the outer appearance of the imaging diagnostic system.

As shown in FIG. 3, CT angiography apparatus 400 includes imaging diagnostic unit 401 serving as a mechanism for performing imaging and imaging control unit 402 such that imaging diagnostic unit 401 and imaging control unit 402 are wire-connected through communication network 403.

Imaging diagnostic unit 401 shoots diagnostic images of a patient. Imaging control unit 402 controls the operation of imaging diagnostic unit 401.

Figure 5:
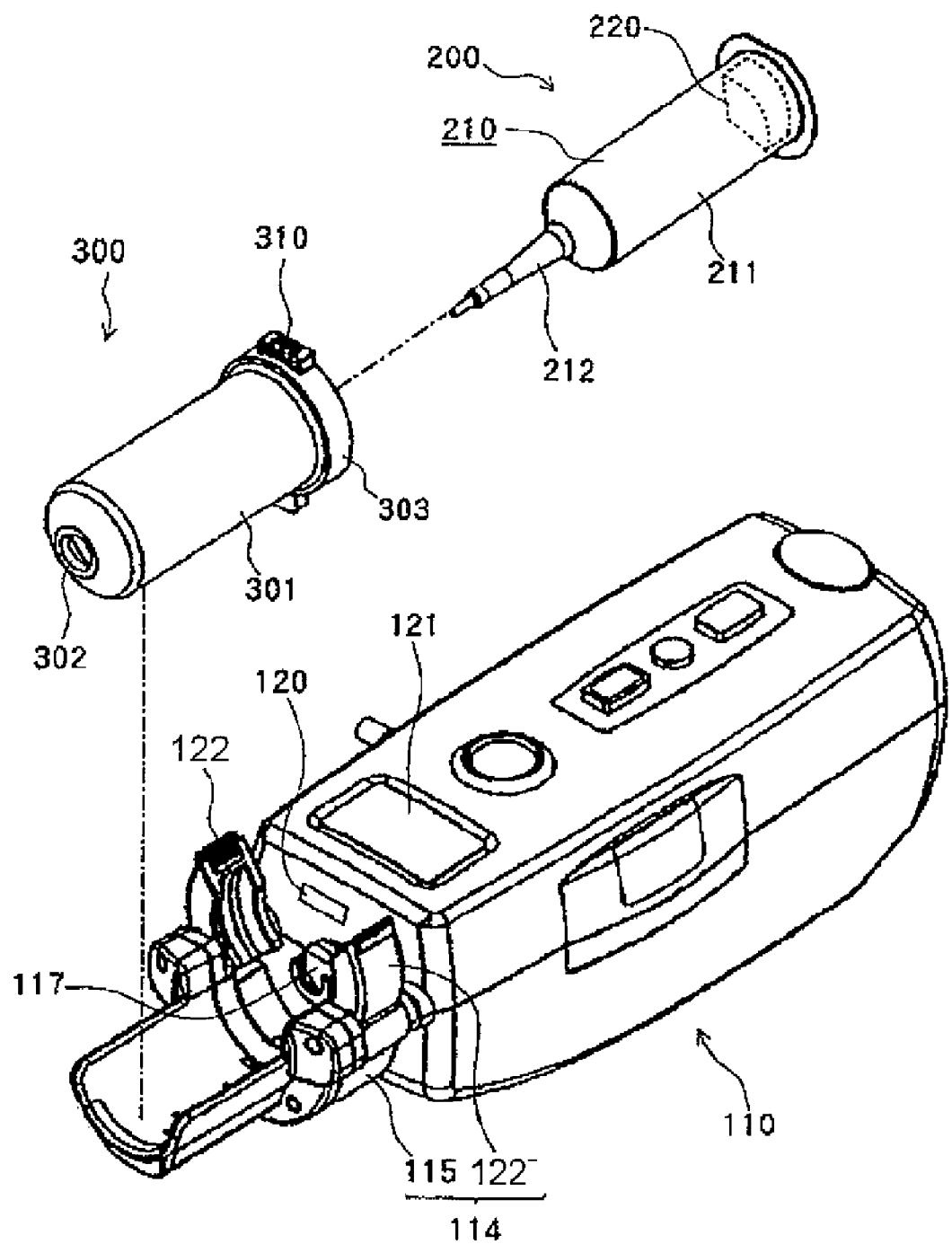
FIG. 5 is a perspective view showing how to mount a chemical solution syringe on an injection execution head of the chemical solution injector with a pressure-resistant cover which is a consumable part.

As shown in FIG. 5, chemical solution syringe 200 comprises cylinder member 210 and piston member 220 wherein piston member 220 is slidably inserted into cylinder member 210. Cylinder member 210 includes cylindrical hollow body 211 which has conduit 212 formed at its closed front end surface. The trailing end of body 211 of cylinder member 210 is opened, and piston member 220 is inserted from the opening into the interior of body 211.

Pressure-resistant cover 300 includes cylindrical hollow body 301 which has through-hole 302 at its closed front end surface. The trailing end of pressure-resistant cover 300 is opened, and cylinder member 210 of chemical solution syringe 200 is inserted from the opening into the interior of body 301.

Pressure-resistant cover 300 has annular cover flange 303 integrally formed on the outer circumference of the trailing end. RFID chip 310 serving as a consumption storage means is put on the upper surface of cover flange 303. RFID chip 310 has data fixedly recorded thereon, such as the identification code for each product type of the pressure-resistant cover 300, the life limit and the like. RFID chip 310 has the consumption degree of pressure-resistant cover 300 rewritably stored thereon, although described later in detail.

Figure 4:
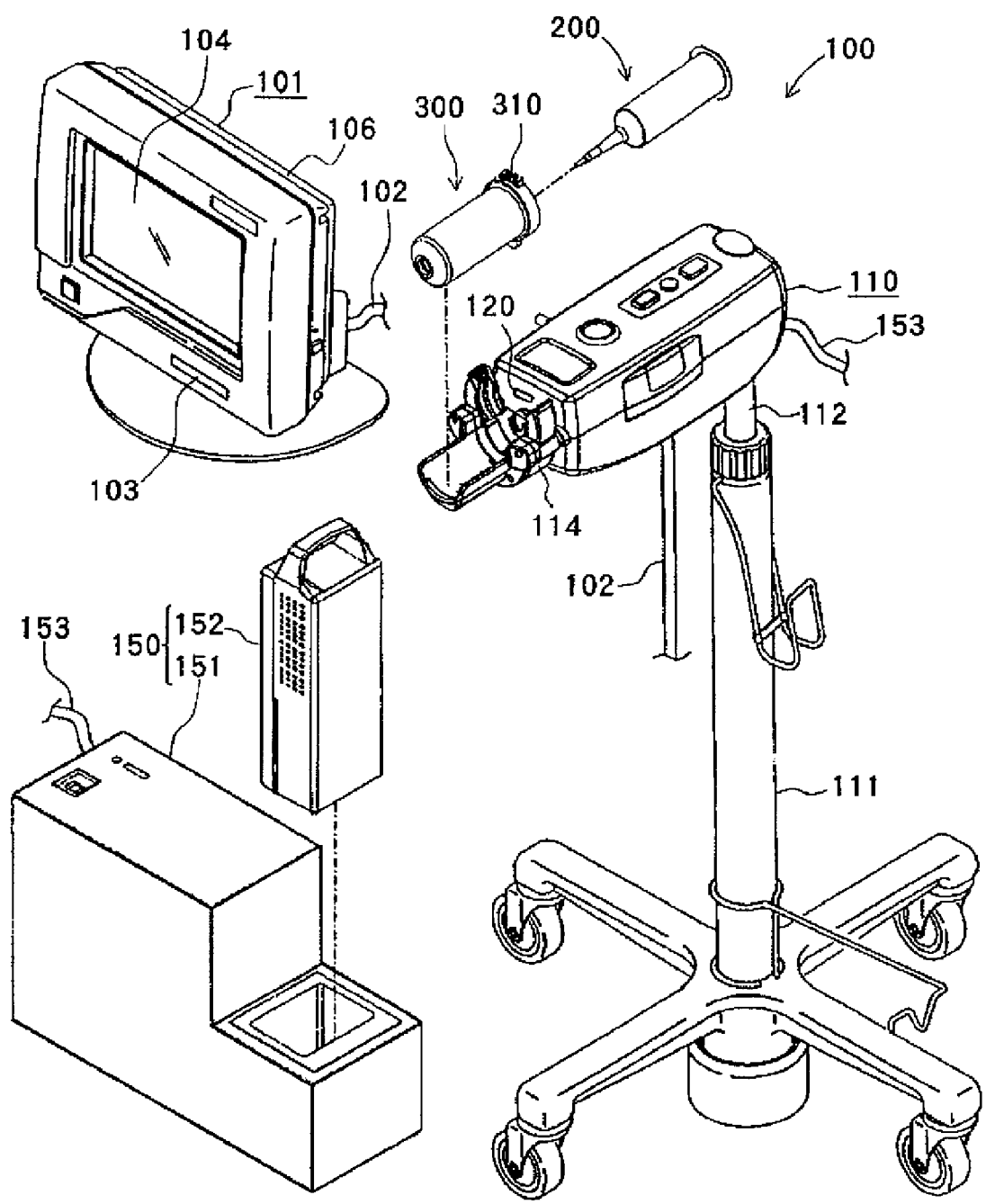
FIG. 4 is a perspective view showing the outer appearance of a chemical solution injector.

As shown in FIG. 4, chemical solution injector 100 of the embodiment includes injection control unit 101' and injection execution head 110 which are constructed as separate components. Injection control unit 101 and injection execution head 110 are wire-connected through communication cable 102. Injection execution head 110 is attached to the top end of caster stand 111 by movable arm 112. Head body 113 of injection execution head 110 has flange holding mechanism 114 on the front surface thereof for removably holding pressure-resistant cover 300 as well as chemical solution syringe 200.

As shown in FIG. 5, flange holding mechanism 114 includes semicircular fixed holding member 115 fixed to a lower portion of the front surface of head body 113 and paired movable holding members 122 individually supported to be pivotable upward and downward at the left and right ends of fixed holding member 115. Cover flange 303 of pressure-resistance cover 300 is fitted into fixed holding member 115 from above, and the upper portion of cover flange 303 is held from above by paired movable holding members 122 on the left and right. The portion of cover flange 303 where RFID chip 310 is protrudes upward, and is located in the space between paired movable holding members 122.

Injection execution head 110 includes piston-driving mechanism 117 placed on the front surface at the center on the inner side of flange holding mechanism 114. Piston driving mechanism 117 holds and presses piston member 220 of chemical solution syringe 200 into cylinder member 210. Piston driving mechanism 117 includes driving motor 118 as a driving source and slides piston member 220 with a screw mechanism (not shown). Load cell 119 serving as an output detecting means is also contained in piston driving mechanism 117 and detects the pressure applied to piston member 220 by piston driving mechanism 117.

Injection execution head 110 has RFID reader/writer 120, serving as data reading/writing means placed on the front surface in the space between closed paired movable holding members 122 on the left and right. Although described later in detail, RFID reader/writer 120 reads various data from RFID chip 310 on pressure-resistance cover 300, and writes the data of the consumption degree to RFID chip 310. Injection execution head 110 also has a sub liquid crystal panel 121 placed in the forward section of the upper surface. Various guidance messages and the like are output as display on sub liquid crystal panel 121.

Figure 2:
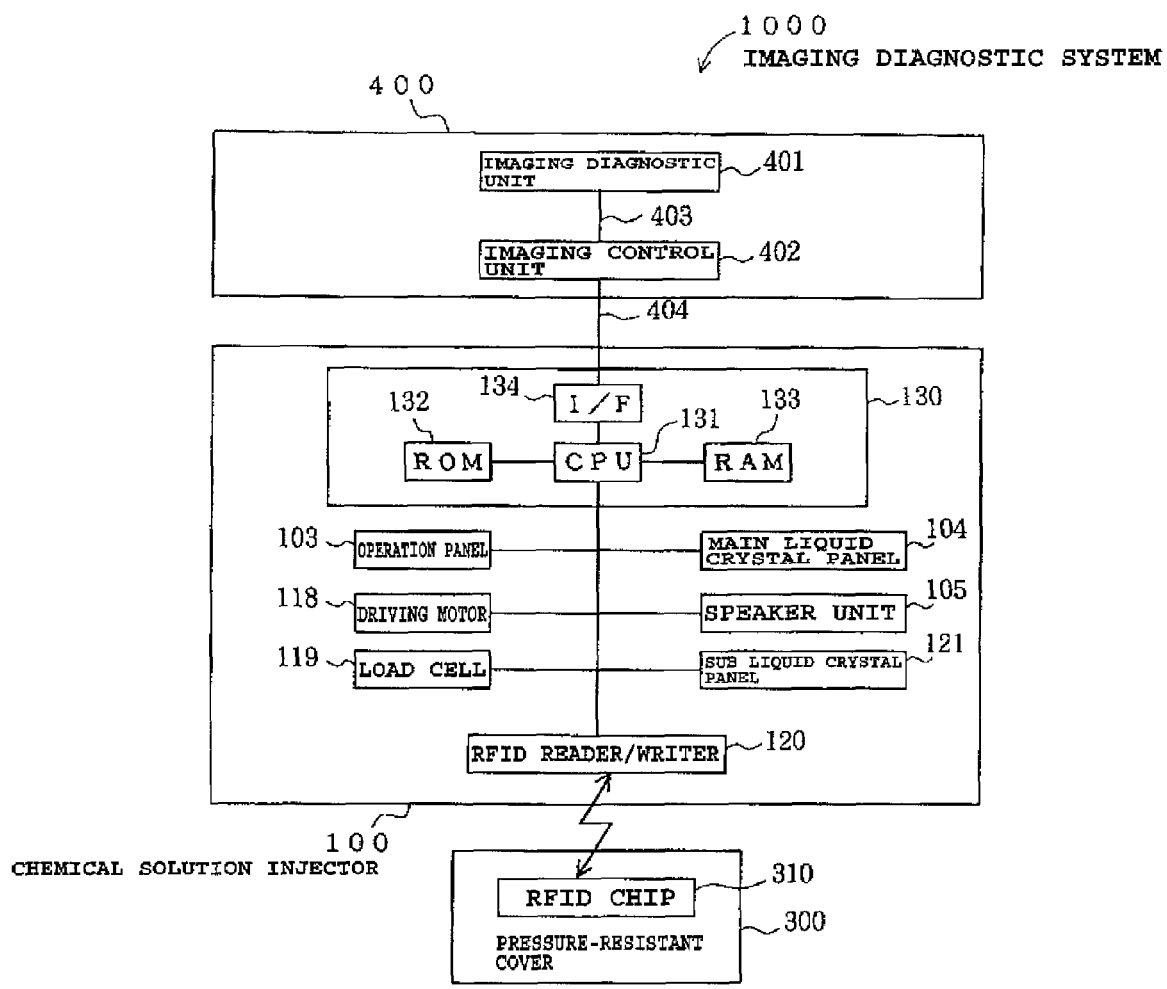
FIG. 2 is a block diagram showing the circuit structure of the imaging diagnostic system.

Injection execution head 110 as described above is wire-connected to injection control unit 101, which controls the operation of injection execution head 110. As shown in FIG. 2, injection control unit 101 contains computer unit 130 and is wire-connected to imaging control unit 402 of CT angiography apparatus 400 through communication network 404. Injection control unit 101 has operation panel 103, main liquid crystal panel 104, speaker unit 105 and the like, all of which are disposed on the front face of unit housing 106. The abovementioned various devices are connected to computer unit 130.

Computer unit 130 is formed of a so-called one-chip microcomputer provided with hardware such as CPU (Central Processing Unit) 131, ROM (Read Only Memory) 132, RAM (Random Access Memory) 133, I/F (Interface) 134 and the like. Computer unit 130 has an appropriate computer program installed as firmware or the like on an information storage medium such as ROM 132, and CPU 131 executes various processing in accordance with the computer program.

Figure 1:
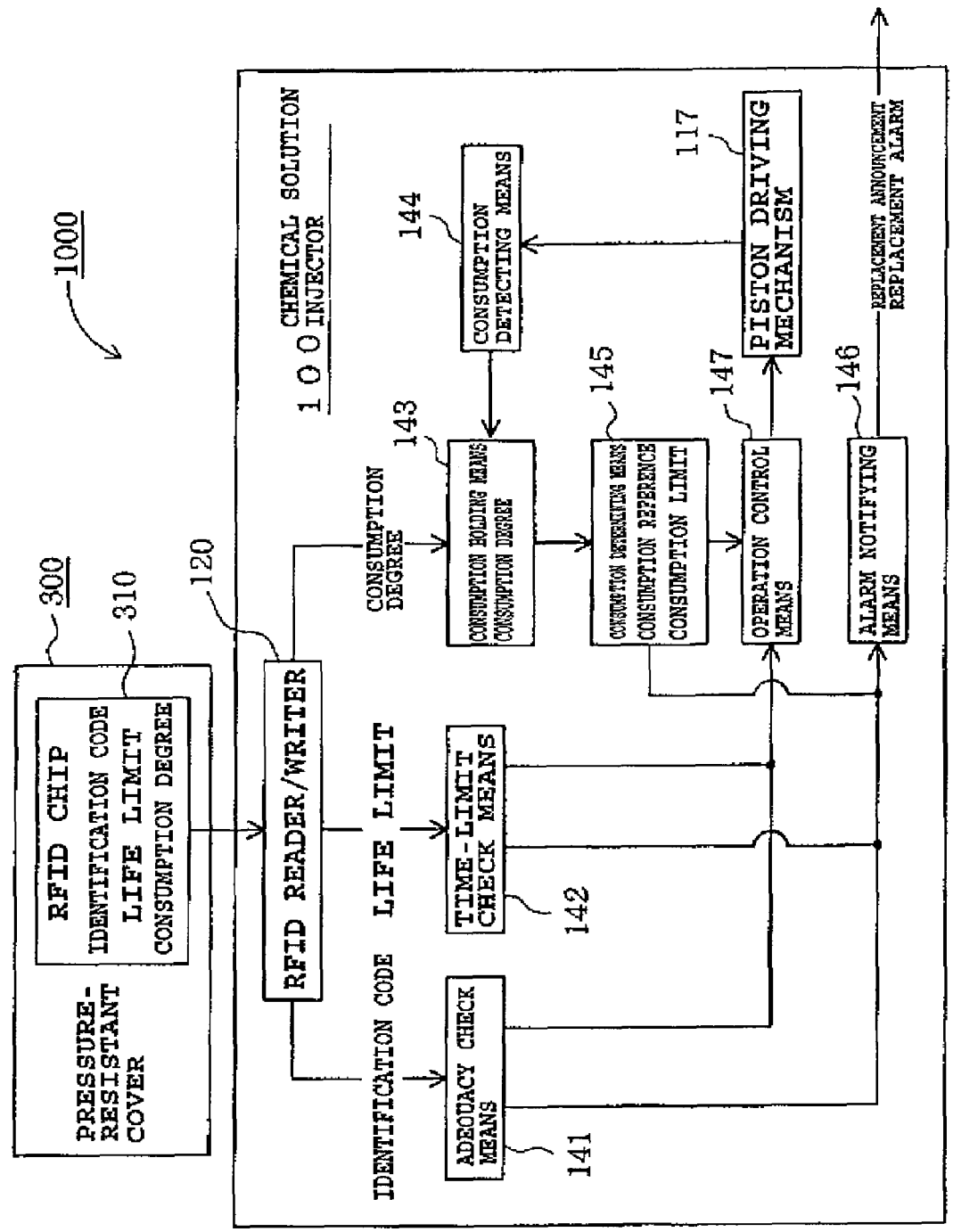
FIG. 1 is a schematic block diagram showing the logical structure of an imaging diagnostic system which is a mechanical system of an embodiment of the present invention.

In chemical solution injector 100 of the embodiment, computer unit 130 operates in accordance with the computer program installed as described above to logically have various means such as adequacy check means 141, time-limit check means 142, consumption holding means 143, consumption detecting means 144, consumption determining means 145, alarm notifying means 146, and operation control means 147, as shown in FIG. 1.

In chemical solution injector 100 of the embodiment, when pressure-resistant cover 300 is attached on injection execution head 110 by flange holding mechanism 114, RFID chip 310 on pressure-resistant cover 300 is opposed to RFID reader/writer 120, then the RFID reader/writer 120 receives various data from RFID chip 310.

Adequacy check means 141 corresponds to the function of CPU 131 which compares the recorded data read from RFID chip 310 with data recorded on ROM 132 in accordance with the computer program installed on ROM 132 or the like. Adequate check means 141 compares the identification code for each product type wirelessly received from RFID chip 310 by RFID reader/writer 120 with the identification code previously recorded as data, to determine whether the received identification code is adequate or not.

Time-limit check means 142 corresponds to the function of CPU 131 which compares the recorded data read from RFID chip 310 with predetermined data in accordance with the computer program, and compares the life limit wirelessly received from RFID chip 310 with the current date, to determine the adequacy.

Consumption holding means 143 corresponds to the function of CPU 131, which temporarily holds on RAM 133 the recorded data on RFID chip 310 in accordance with the computer program, and temporarily holds the consumption degree wirelessly received from RFID chip 310. Consumption detecting means 144 corresponds to the function of CPU 131, which updates the stored data on RAM 133 in accordance with the computer program and the output data from load cell 119, and updates the data of the consumption degree temporarily held by consumption holding means 143, in accordance with the operation of piston driving mechanism 117.

More specifically, in chemical solution injector 100 of the embodiment, an operator makes some entries in an injection program or the like on operation panel 103 as desired to cause piston driving mechanism 117 to press piston member 220 of chemical solution syringe 200 into cylinder member 210 at a variable pressure.

The pressure is detected in real time by load cell 119. The data of the pressure is acquired by CPU 131 once in a predetermined unit time, and it is recorded on RAM 133. CPU 131 sequentially adds up the pressure in each unit time as the consumption degree, to update the data of the consumption degree wirelessly received from RFID chip 310.

For example, when piston driving mechanism 117 presses piston member 220 of chemical solution syringe 200 at a pressure of 5 kg, the number "5", is accumulated as the consumption degree every one second. When piston driving mechanism 117 presses piston member 220 of chemical solution syringe 200 at a pressure of 10 kg, the number "10" is accumulated as the consumption degree every one second.

By way of example, when one injection operation is generally performed at a pressure of 5 kg for 10 minutes, and after the injection operation is repeated 100 times, pressure-resistant cover 300 needs to be replaced, since the average consumption degree in one injection operation is 3000, a consumption limit is set to 300000 and a consumption reference is set to 290000. Naturally zero is set as the consumption degree by default on RFID chip 310 of new pressure-resistant cover 300.

Consumption determining means 145 corresponds to the function of CPU 131 which compares stored data on RAM 133 with stored data on ROM 132 in accordance with the computer program, and determines whether or not the consumption degree, temporarily held by consumption holding means 143 and updated by consumption detecting means 144, exceeds the lower consumption reference or the higher consumption limit per unit time.

Alarm notifying means 146 corresponds to the function of CPU 131 which outputs the stored data on ROM 132 to main/sub liquid crystal panels 104, 121 or from speaker unit 105 in accordance with the computer program, and outputs and notifies various guidance messages in accordance with the determination results of adequacy check means 141, time-limit check means 142, and consumption determining means 145.

More specifically, in chemical solution injector 100 of the embodiment, when the identification code wirelessly received from RFID chip 310 by RFID reader/writer 120 is not registered on ROM 132, a guidance message, for example "This pressure-resistant cover is inappropriate and unusable" is notified with text display on main/sub liquid crystal panels 104, 121, or with sound output from speaker unit 105.

When the life limit wirelessly received from RFID chip 310 by RFID reader/writer 120 is before the current date, a guidance message, for example "Life limit is exceeded and this pressure-resistant cover is unusable" is notified on main/sub liquid crystal panels 104, 121 or from speaker unit 105.

When the consumption limit wirelessly received from RFID chip 310 by RFID reader/writer 120 exceeds the consumption reference, and when the consumption limit updated in real time in accordance with the operation of piston driving mechanism 117 reaches the consumption reference, a guidance message, for example "Consumption limit is approaching for this pressure-resistant cover. This is the final use, and use new one next time" is notified as a replacement announcement on main/sub liquid crystal panels 104, 121 or from speaker unit 105.

When the consumption limit wirelessly received from RFID chip 310 by RFID reader/writer 120 exceeds the consumption limit, and when the consumption limit updated in real time in accordance with the operation of piston driving mechanism 117 reaches the consumption limit, a guidance message, for example "This pressure-resistant cover reaches consumption limit and is unusable" is notified as a replacement alarm on main/sub liquid crystal panels 104, 121 or from speaker unit 105.

Operation control means 147 corresponds to the function of CPU 131, which controls the operation of driving motor 118 of piston driving mechanism 117 in accordance with the computer program. When adequacy means 141 determines that the identification code is inadequate, when time-limit check means 142 determines that the life limit is exceeded, and when consumption determining means 145 determines that the consumption limit exceeds the consumption limit, operation control means 147 disables piston driving mechanism 117.

Although the abovementioned various means of chemical solution injector 100 are accomplished by pieces of hardware such as main/sub liquid crystal touch panels 104, 121 as required, they are mainly implemented by CPU 131 as a piece of hardware functioning in accordance with the resources and the computer program stored on an information storage medium such as ROM 132.

The computer program is stored on an information storage medium such as RAM 133 as software for causing CPU 131 or the like, to perform processing operations including the comparison of the wirelessly received identification code for each product type with the previously registered identification code to determine the adequacy when the various data are wirelessly received from RIFD chip 310 by RFID reader/writer 120, the comparison of the wirelessly received life limit with the current date to determine the adequacy, the temporal holding of the wirelessly received consumption degree on RAM 133, the update of the data of the wirelessly held consumption degree in accordance with the operation of piston driving mechanism 117, the determination whether or not the temporarily held and updated consumption degree exceeds the lower consumption reference and the higher consumption limit per unit time, the output and notification of the guidance messages on main/sub liquid crystal panels 104, 121 and from speaker unit 105 when the wirelessly received identification code for each product type is not registered as data, when the wirelessly received life limit is before the current date, when the wirelessly received consumption limit exceeds the consumption reference, when the consumption limit updated in real time in accordance with the operation of piston driving mechanism 117 reaches the consumption reference, when the wirelessly received consumption limit exceeds the consumption limit, and when the consumption limit updated in real time in accordance with the operation of piston driving mechanism 117 reaches the consumption limit, and the disablement of piston driving mechanism 117 when the identification code is determined to be inadequate, when the life limit is determined to be exceeded, and when the consumption limit is determined to exceed the consumption limit.

As shown in FIG. 4, chemical solution injector 100 of the embodiment includes power supply unit 150, which is wire-connected to injection execution head 110. Power supply unit 150 includes a battery stand 151 and a secondary battery 152. Secondary battery 152 is removably mounted on battery stand 151 wire-connected to injection execution head 110 through current-carrying cable 153.

[Operation of the Embodiment]

When chemical solution injector 100 of the embodiment is used in the abovementioned structure, chemical solution injector 100 is disposed near imaging unit 401 of CT angiography apparatus 400, and chemical solution syringe 200, pressure-resistant cover 300, and an extension tube (not shown) are prepared for use, as shown in FIG. 3.

Next, as shown in FIGS. 4 and 5, chemical solution syringe 200 is inserted into pressure-resistant cover 300 and then connected to a patient (not shown) through the extension tube. Cover flange 303 of pressure-resistant cover 300 is inserted into opened flange holding mechanism 114 of injection execution head 110.

Figure 6:
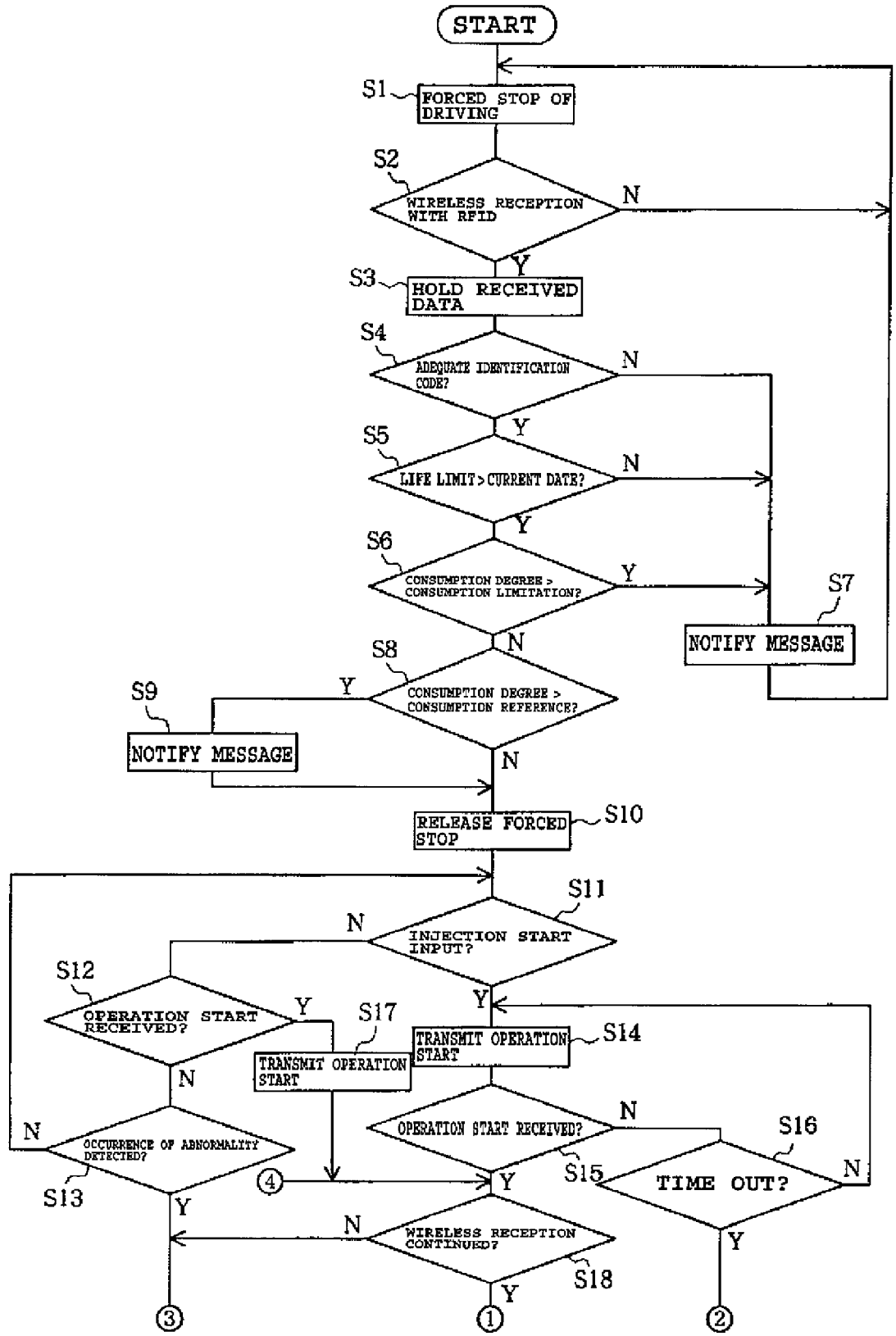
FIG. 6 is a flow chart showing the first half of processing operation in the chemical solution injector.

Flange holding mechanism 114 is closed to oppose RFID chip 310 on pressure-resistant cover 300 to RFID reader/writer 120 on injection execution head 110. Then, as shown in FIG. 6, while chemical solution injector 100 controls piston-driving mechanism 117 to be inoperative (step S1), it wirelessly receives various data from RFID chip 310 by RFID reader 120 (step S2).

The various data wirelessly received from the RFID chip 310 are temporarily held by RAM 133 (step S3). The identification code of pressure-resistant cover 300 is detected from the temporarily held received data and is compared with the identification code previously registered as data, to determine whether the identification code is adequate or not (step S4).

When the identification code is determined to be inadequate, the guidance message, for example "This pressure-resistant cover is inappropriate and unusable" is notified with display output on main/sub liquid crystal panels 104, 121 and with sound output from speaker unit 105 (step S7). Chemical solution injector 100 returns to the initial state in which it controls piston-driving mechanism 117 to be inoperative (step S1).

On the other hand, when the identification code is determined to be adequate (step S4), the life limit of pressure-resistant cover 300 is detected from the received data, and it is compared with the current date to determine the adequacy (step S5). When the life limit is before the current date, the guidance message, for example "Life limit is exceeded and this pressure-resistant cover is unusable" is notified on main/sub liquid crystal panels 104, 121 and from speaker unit 105 (step S7). Chemical solution injector returns to the initial state (step S1).

When the life limit is after the current date (step S5), the consumption degree of pressure-resistant cover 300 is detected from the received data, and it is compared with the predetermined consumption limit (step S6). When the consumption degree exceeds the consumption limit, the guidance message, for example "Consumption limit is exceeded and this pressure-resistant cover is not usable" is notified as a replacement alarm on main/sub liquid crystal panels 104, 121 and from speaker unit 105 (step S7). Chemical solution injector 100 returns to the initial state (step S1).

On the other hand, when the consumption degree does not exceed the consumption limit (step S6), the consumption degree is compared with the predetermined consumption reference (step S8). When the consumption degree exceeds the consumption reference, the guidance message, for example "Consumption limit is approaching for this pressure-resistant cover. This is the final use, and use new one next time" is notified as a replacement announcement on main/sub liquid crystal panels 104, 121 and from speaker unit 105 (step S9).

When the comparison between the consumption degree and the consumption reference is completed (steps S8, S9), piston-driving mechanism 117 is controlled to be operative (step S10). In this state, an operator makes entry to start operation to main/sub touch panels 104, 121 or operation panel 103. Chemical solution injector 100 detects the entry (step S11) and transmits data for starting operation to CT angiography apparatus 400 (step S14).

Figure 8:
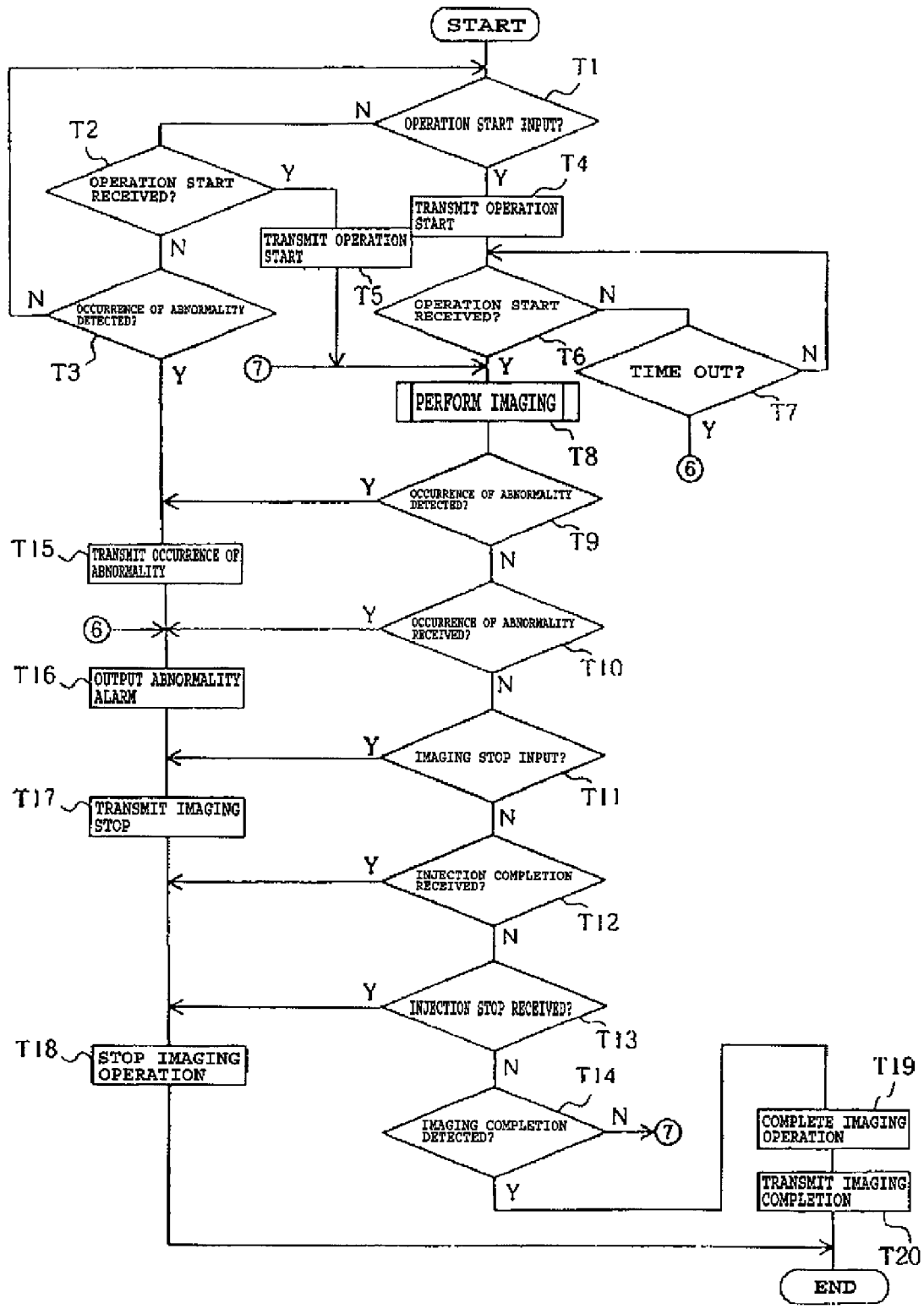
FIG. 8 is a flow chart showing processing operation in a CT angiography apparatus.

Referring to FIG. 8, CT angiography apparatus 400 receives the data for staring operation from chemical solution injector 100 (step T2) and transmits the data for starting operation back to chemical solution injector 100 and performs imaging operation (step T8). Thus, in imaging diagnostic system 1000 of the embodiment, the imaging of CT angiography apparatus 400 follows the chemical solution injection of chemical solution injector 100.

As shown in FIGS. 6 and 8, in imaging diagnostic system 1000 of the embodiment, when chemical solution injector 100 is ready as described above (steps S11 to S13) and the operator makes entry to start operation to CT angiography apparatus 400 (step T1), the chemical solution injection of chemical solution injector 100 follows the imaging of CT angiography apparatus 400 (steps T4, T6 and subsequent steps, steps S12, S18 and subsequent steps).

Figure 7:
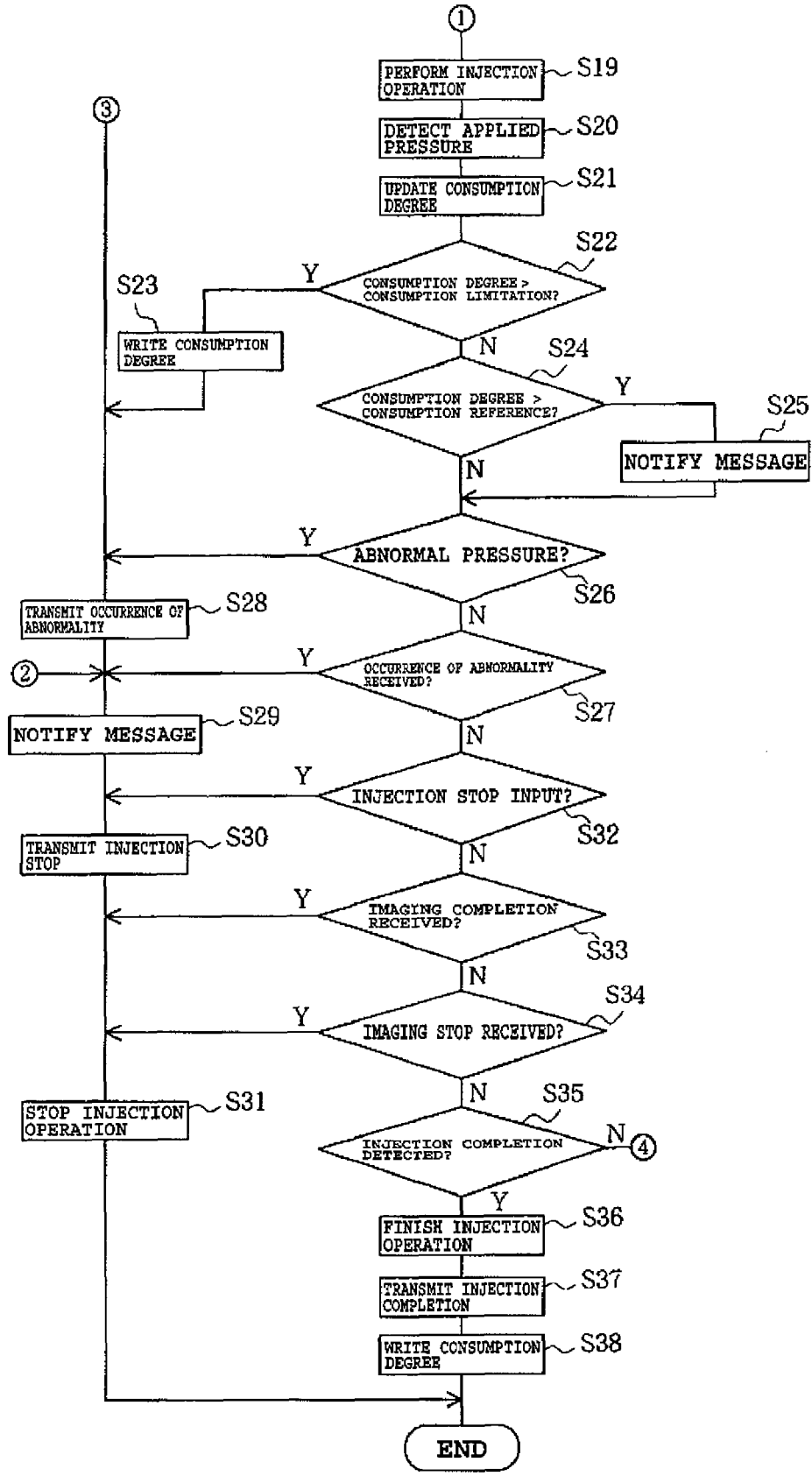
FIG. 7 is a flow chart showing the latter half of the processing operation.

As shown in FIG. 7, in chemical solution injector 100 of the embodiment, when piston-driving mechanism 117 is driven to perform chemical solution injection (step S19), the data of the pressure detected by load cell 119 is acquired by computer unit 130 per unit time such as one second (step S20).

The acquired data of the pressure is added as the new consumption degree to the temporarily held consumption degree (step S21). The consumption degree updated by the addition is compared with the consumption limit (step S22). When the consumption degree exceeds the consumption limit, the guidance message, for example "Consumption limit is exceeded and this pressure-resistant cover is not usable" is notified as the replacement alarm on main/sub liquid crystal panels 104, 121 and from speaker unit 105 (step S29).

Chemical solution injector 100 transmits the data of the occurrence of abnormality and the data of stop of injection to CT angiography apparatus 400 (steps S28 and S31), and forcedly stops piston-driving mechanism 117 (step S31). As a result, the injection operation is not continued while the consumption degree of pressure-resistant cover 300 exceeds the consumption limit.

When the consumption degree exceeds the consumption limit as described above, the consumption degree exceeding the consumption limit is written as data to RFID chip 310 on pressure-resistant cover 300 by RFID reader/writer 120 (step S23). If pressure-resistant cover 300 is mounted next on chemical solution injector 100, the fact that the consumption degree exceeds the consumption limit is immediately detected as shown in FIG. 6 (step S6), so that piston-driving mechanism 117 is not driven (step S1).

On the other hand, in CT angiography apparatus 400, when the data of the occurrence of the abnormality is received (step T10), the occurrence of abnormality is output and notified as a check alarm with guidance display or the like (step T16) as shown in FIG. 8. When the stop of operation is received (step T13), the imaging operation is stopped (step T18).

As shown in FIG. 7, in chemical solution injector 100, when the consumption degree updated by the driving of piston driving mechanism 117 exceeds the consumption reference and does not exceed the consumption limit (steps S20 to S24), the guidance message, for example "Consumption limit is approaching for this pressure-resistant cover. This is the final use, and use new one next time" is notified as the replacement announcement on main/sub liquid crystal panels 104, 121 and from speaker unit 105 (step S25).

During the driving of chemical solution syringe 200 by piston driving mechanism 117, RFID chip 310 thereon is continuously detected by RFID reader/writer 120 (step S18). If the abovementioned detection is stopped (step S18) before the completion of the injection operation (step S35), the injection operation by piston driving mechanism 117 is stopped (step S31).

The guidance message, for example "Syringe removal is detected. Make sure syringe is put appropriately" is notified as a check alarm on main/sub liquid crystal panels 104, 121 and from speaker unit 105 (step S29). The occurrence of abnormality and the stop of injection are transmitted to CT angiography apparatus 400 (steps S28 and S31).

Then, CT angiography apparatus 400 receives data representing the occurrence of abnormality (step T10) and outputs the occurrence of abnormality as a check alarm with guidance display or the like (step T16). When it receives the data representing the stop of operation (step T13), the imaging operation is stopped (step T18).

In chemical solution injector 100 and CT angiography apparatus 400 of the embodiment, when the occurrence of abnormality is detected in the abovementioned ready state (steps S13 and T3) or when the occurrence of abnormality is detected during the operation (steps S26 and T9), the occurrence of abnormality is output and notified (steps S29 and T16) and the operation is stopped (steps S31 and T18).

Since the occurrence of abnormality in one of them is transmitted to the other (steps S28 and T15), the other receives the data (steps T10 and S27) and then outputs and notifies the occurrence of abnormality (steps T16 and S29). Since the operation stop in one of them is transmitted to the other (steps S30 and T17), the other receives the data (steps T13 and S34) and also stops the operation (steps T18 and S31).

When one of them receives entry to stop operation (steps S32 and T11), the one stops the operation (steps S31 and T18) and transmits it to the other (steps S30 and T17). The other receives the data (steps T13 and S34) and stops the operation (steps T18 and S31).

When the completion of the operation is detected in one of them (steps S35 and T14), the operation is ended (steps S36 and T19) and the end of the operation is transmitted to the other (steps S37 and T20). The other receives the data (steps T12 and S34) and stops the operation (steps T18 and S31).

In chemical solution injector 100 of the embodiment, when the injection operation is finished normally as described above (step S36), the updated consumption degree is written to RFID chip 310 on chemical solution syringe 200 by RFID reader/writer 120 on injection execution head 110 (step S38).

[Effect of the Embodiment]

In imaging diagnostic system 1000 of the embodiment, when pressure-resistant cover 300 as a consumable part is mounted on chemical solution injector 100, RFID reader/writer 120 of chemical solution injector 100 reads the consumption degree from RFID chip 310 on pressure-resistant cover 300 and the read consumption degree, and it is compared with the consumption limit and the consumption reference.

If the consumption degree of pressure-resistant cover 300 exceeds the consumption reference, that is notified to the operator, thus the operator can recognize appropriately the consumption degree of pressure-resistant cover 300. This can prevent the continued use of consumed pressure-resistant cover 300 or unnecessary replacement of pressure-resistant cover 300 which has not been used up.

When the consumption degree of pressure-resistant cover 300 exceeds the consumption limit, piston-driving mechanism 117 of chemical solution injector 100 is controlled to be inoperative. Thus, even when pressure-resistant cover 300 with the consumption degree exceeding the consumption limit is mounted, piston driving mechanism 117 of chemical solution injector 100 does not operates, and any breakage of pressure-resistant cover 300 during injection operation can be automatically prevented. In addition, since the operator is notified of the fact that the consumption degree of pressure-resistant cover 300 exceeds the consumption limit, the operator can appropriately recognize the consumption degree of pressure-resistant cover 300 and replace that pressure-resistant cover 300 with a new one.

When pressure-resistant cover 300 with the consumption degree not exceeding the consumption limit is mounted on chemical solution injector 100 to perform the injection operation, the data of the consumption degree is updated in accordance with the operation of piston driving mechanism 117. If the updated consumption degree exceeds the consumption reference, the operator is also notified of that fact, thus the operator can favorably recognize the consumption degree of pressure-resistant cover 300 reaching the consumption reference during the injection operation.

When the updated consumption degree exceeds the consumption limit, the operator is also notified of that fact, so that the operator can favorably recognize the consumption degree of pressure-resistant cover 300 reaching the consumption limit during the injection operation. Since piston driving mechanism 117 is also forcedly stopped, the operation of piston driving mechanism 117 is not continued while the consumption degree of pressure-resistant cover 300 exceeds the consumption limit, thereby automatically preventing any breakage of pressure-resistant cover 300 during the injection operation.

In imaging diagnostic system 1000 of the embodiment, only when cover flange 303 of pressure-resistant cover 300 is appropriately held by flange holding mechanism 114 of injection execution head 110, RFID chip 310 on pressure-resistant cover 300 is opposed to RFID reader/writer 120 on injection execution head 110, to allow wireless communication between RFID chip 310 and RFID reader/writer 120.

This structure prevents the situation in which pressure-resistant cover 300 is not appropriately mounted on injection execution head 110 and piston driving mechanism 117 is operated to cause pressure-resistant cover 300 to come off. Chemical solution injector 100 forcedly stops the operation of piston driving mechanism 117 when the wireless communication between RFID chip 310 and RFID reader/writer 120 is interrupted during the injection operation. For example if pressure-resistant cover 300 comes off during the injection operation, piston-driving mechanism 117 can automatically be stopped forcedly.

Since the mechanism for detecting the removal of pressure-resistant cover 300 is formed of RFID chip 310 and RFID reader/writer 120 provided for transferring the various data to chemical solution injector 100, the removal of pressure-resistant cover 300 can be detected with the simple structure without requiring a dedicated sensor mechanism.

In imaging diagnostic system 1000 of the embodiment, the data of the consumption degree of pressure-resistant cover 300 is managed by RFID chip 310 put on pressure-resistant cover 300 itself. For example, when a plurality of pressure-resistant covers 300 are simultaneously used in a medical facility, each data of the consumption degree can be managed automatically without requiring complicated operation.

In imaging diagnostic system 1000 of the embodiment, since the consumption degree of pressure-resistant cover 300 is calculated based on both of the pressure applied to pressure-resistant cover 300 and the time period over which the pressure is applied, the consumption degree can be properly calculated. Particularly, the consumption degree is calculated by accumulating the pressure per unit time and thus does not need complicated processing or the like.

Chemical solution injector 100 of the embodiment outputs the check alarm and forcedly stops the injection operation when the pressure applied to piston member 220 of chemical solution syringe 200 reaches the abnormal level. This can prevent any medical malpractice of injection of a chemical solution at an abnormal pressure. In other words, the pressure applied to piston member 220 is used both to prevent the chemical solution injection at an abnormal pressure and to calculate the consumption degree of pressure-resistant cover 300, thereby providing high use efficiency of the device.

In imaging diagnostic system 1000 of the embodiment, the data of the life limit of pressure-resistant cover 300 is registered on RFID chip 310, and chemical solution injector 100 does not operate piston driving mechanism 117 when the current date is after the life limit, which automatically prevents the injection operation with pressure-resistant cover 300 after the expiration of the life limit. Since the operator is notified of the fact that the life limit of pressure-resistant cover 300 is exceeded in this case, the operator can replace pressure-resistant cover 300 after the expiration of the life limit with new pressure-resistant cover 300.

In imaging diagnostic system 1000 of the embodiment, the identification code for each pressure-resistant cover 300 is registered on RIFD chip 310, and chemical solution injector 100 does not operate piston driving mechanism 117 if its identification code is not registered. This automatically prevents the injection operation with inappropriate pressure-resistant cover 300. Since the operator is notified of the fact that pressure-resistant cover 300 is inappropriate, the operator can replace inappropriate pressure-resistant cover 300 with appropriate pressure-resistant cover 300.

In imaging diagnostic system 1000 of the embodiment, sub liquid crystal panel 121 is placed near flange holding mechanism 114 of injection execution head 110 for holding pressure-resistant cover 300, and the various guidance messages and the like associated with the consumption degree of pressure-resistant cover 300 are output and displayed on sub liquid crystal panel 121. The operator can intuitively recognize the various data relating to the consumption degree of pressure-resistant cover 300.

In imaging diagnostic system 1000 of the embodiment, the various guidance messages and the like associated with the consumption degree of pressure-resistant cover 300 are also output and displayed on main liquid crystal panel 104 of injection control unit 101 for controlling the operation of injection execution head 110. The operator who manually operates injection control unit 101 can recognize the various data relating to the consumption degree of pressure-resistant cover 300 without fail.

In imaging diagnostic system 1000 of the embodiment, since the chemical solution injection in chemical solution injector 100 is automatically associated with the imaging in CT angiography apparatus 400, the diagnostic images can be taken at the appropriate time from the patient injected with the contrast medium and physiological saline at the appropriate time.

[Modifications of the Embodiment]

The present invention is not in any way limited to the abovementioned embodiment, but various changes and modifications may be made therein without departing from the scope of the invention. For example, in the above embodiment, pressure-resistant cover 300 serving as the cylinder adapter is used as the consumable part and chemical solution injector 100 is used as the mechanical apparatus in which the consumable part is used, but the present invention is applicable to various consumable parts and various mechanical apparatuses.

For example, in an imaging diagnostic system (not shown) in which a chemical solution syringe is directly mounted on a chemical solution injector, the chemical solution syringe may be formed as a consumable part having RFID chip 310 put thereon, and the data of the consumption degree thereof may be read and written by RFID reader/writer 120 of the chemical solution injector.

In addition, in an imaging diagnostic system (not shown) in which a chemical solution syringe is mounted on a chemical solution injector by using a cylinder adapter instead of a pressure-resistant cover, the cylinder adapter may be formed as a consumable part having RFID chip 310 put thereon, and the data of the consumption degree thereof may be read and written by RFID reader/writer 120 of the chemical solution injector.

In a mechanical system (not shown) having secondary battery 152 as a power source of a mechanical device as described above, it is possible, for example, that secondary battery 152 is formed as a consumable part having RFID chip 310 put thereon, and the data of the consumption degree thereof is read and written by RFID reader/writer 120 mounted on battery stand 151. In this case, the consumption degree of secondary batter 152 may be calculated as the number of uses of secondary battery 152, the operating time of secondary battery 152, the product of the operating time of secondary battery 152 and the power consumption of the mechanical device, or the like.

The mechanical system having secondary battery 152 as the power source of the mechanical device as described above naturally includes a battery-charging apparatus (not shown) for charging secondary battery 152. For example, it is possible that secondary battery 152 is formed as a consumable part having RFID chip 310 put thereon and the data of the consumption degree thereof is read and written by RFID reader/writer 120 mounted on the battery-charging apparatus. In this case, the consumption degree of secondary battery 152 may be calculated as the number of charges of secondary battery 152, the charge time of secondary battery 152, or the like.

In the above embodiment, the consumption degree of pressure-resistant cover 300 is calculated by both of the applied pressures and the operating time. For example, only the operating time or the number of uses may be employed as the consumption degree. The accuracy of the calculation of the consumption degree is reduced in this case, but the data processing is performed more simply.

In the above embodiment, the consumption degree of pressure-resistant cover 300 is assumed to be directly proportional to the pressure and the time, and the consumption degree of pressure-resistant cover 300 is calculated by accumulating the pressure per unit time. When the consumption degree of pressure-resistant cover 300 is not directly proportional to the pressure and the time, the consumption degree may be calculated, for example, through predetermined processing by using the pressure and the time.

For example, when an increase in the pressure or the time causes an increase in the consumption degree at an accelerated pace, the consumption degree may be calculated with the square of the pressure or the time or by using a table which defines the consumption degree in each unit time, for example as one at a pressure of less than three kg, two at a pressure from 3 to 6 kg, four at a pressure from 6 to 9 kg, and eight at a pressure of more than 9 kg.

In the above embodiment, the pressure applied to piston member 220 of chemical solution syringe 200 by piston driving mechanism 117 is used as the pressure used to calculate the consumption degree of pressure-resistant cover 300. Alternatively, the pressure of the chemical solution injected into the patient from chemical solution syringe 200 may be used as the pressure used to calculate the consumption degree of pressure-resistant cover 300.

For example, when only one type of chemical solution syringe 200 and only one type of pressure-resistant cover 300 are mounted on chemical solution injector 100, the stress applied to press piston member 220 by piston driving mechanism 117 is proportional to the pressure of the chemical solution in a one-to-one relationship. If various types of chemical solution syringes 200 and pressure-resistant covers 300 are mounted on chemical solution injector 100, the stress applied by piston driving mechanism 117 is not proportional to the pressure of the chemical solution.

In such a case, the pressure of the chemical solution may be detected by placing a pressure sensor (not shown) on chemical solution syringe 200 or an extension tube, for example. It is also possible that various types of data including the area of the front surface of piston member 220 and the viscosity of the chemical solution are wirelessly transmitted from RFID chip 310 on pressure-resistant cover 300 to chemical solution injector 100, and the pressure of the chemical solution is calculated from the stress applied by piston driving mechanism 117 based on the various types of data.

In the above embodiment, not only the consumption degree but also the identification code and the life limit are registered as the data on RFID chip 310 of pressure-resistant cover 300. Only the consumption degree may be written on RFID chip 310 such that it can be updated, or various types of data other than the abovementioned data including the identification data may be registered on RFID chip 310.

In the above embodiment, the consumption reference and the consumption limit of pressure-resistant cover 300 are previously registered in chemical solution injector 100. The consumption reference and the consumption limit may be previously registered fixedly on RFID chip 310 of pressure-resistant cover 300, and chemical solution injector 100 may compare the consumption reference and the consumption limit read from RFID chip 310 with the consumption degree.

In this case, if pressure-resistant cover 300 has an improved consumption reference or consumption limit due to the use of a new material, the new consumption reference or consumption limit may be registered on RFID chip 310 of pressure-resistant cover 300, and the registered data in chemical solution injector 100 does not need to be updated.

When various types of chemical solution syringes 200 and pressure-resistant covers 300 are mounted on chemical solution injector 100 and the types of chemical solution syringes 200 are associated with the types of pressure-resistant covers 300 in a one-to-one relationship, various types of data of chemical solution syringes 200 and the liquids therein may be registered as data on RFID chip 310 of pressure-resistant cover 300 and used for controlling the injection operation in chemical solution injector 100.

When the various data of chemical solution syringes 200 and the liquids therein may be registered on RFID chip 310 of pressure-resistant cover 300 in this case, the various data may be output and displayed on main/sub liquid crystal displays 104 and 121 to allow the operator to see the various data of the liquids and the like.

In the above embodiment, when the consumption degree of pressure-resistant cover 300 exceeds the consumption limit during the injection operation of chemical solution injector 100, the operation of piston driving mechanism 117 is forcedly stopped. For example, it is also possible that, when the consumption degree of pressure-resistant cover 300 exceeds the consumption limit during the injection operation, a guidance message is only output and the operation of piston driving mechanism 117 is continued, and when the consumption degree of pressure-resistant cover 300 exceeds the consumption limit at the start of the injection operation or at the mounting of pressure-resistant cover 300, piston driving mechanism 117 does not operates.

In this case, since pressure-resistant cover 300 does not need to be replaced during the injection operation, the injection operation can be performed smoothly. In addition, the injection operation is not started with consumed pressure-resistant cover 300, which can favorably prevent any breakage of pressure-resistant cover 300 during the injection operation.

In the above embodiment, chemical solution injector 100 includes one piston driving mechanism 117 and injects only the contrast medium. It is also possible to implement a chemical solution injector (not shown) which includes two piston driving mechanisms 117 to inject a contrast medium and physiological saline or a chemical solution injector (not shown) which includes three or more piston driving mechanisms 117 to inject three types of more of liquids.

In the above embodiment, CT angiography apparatus 400 is used as the imaging diagnostic apparatus, and chemical solution injector 100 injects the contrast medium for CT. For example, it is possible that an MRI apparatus or a PET apparatus is used as the imaging diagnostic apparatus and the chemical solution injector injects a contrast medium.

In the above embodiment, CPU 131 operates in accordance with the computer program stored in RAM 133 or the like to realize logically various means as various functions of chemical solution injector 100. Each of the various means may be formed as specific hardware, or some of them may be stored as software on RAM 133 or the like, while others may be formed as hardware.

The disclosure of the present application is summarized as follows:

1. A mechanical system in which a consumable part is removably mounted on a mechanical device and the consumable part is replaced when its durability is reduced to a predetermined level after the repeated use thereof, comprising:
    a consumption storage means put on the consumable part for storing at least data of a consumption degree such that the consumption degree can be updated,
    wherein the mechanical device includes:
    a part using means for using and operating the consumable part removably mounted thereon;
    a data reading means for reading the data of the consumption degree from the consumption storage means of the mounted consumable part;
    a consumption holding means for temporarily holding the read data of the consumption degree;
    a consumption detecting means for updating the temporarily held data of the consumption degree in accordance with operation of the part using means;
    a consumption determining means for determining whether or not the temporarily held consumption degree exceeds a predetermined consumption reference;
    an alarm notifying means for outputting and notifying a predetermined replacement announcement when it is determined that the consumption degree exceeds the consumption reference; and a data writing means for writing the updated data of the consumption degree to the consumption storage means on the consumable part.

2. The mechanical system according to 1, wherein the mechanical device also includes an operation control means for controlling the part using means to be inoperative when it is determined that the consumption degree exceeds the consumption reference.

3. The mechanical system according to 1, wherein the consumption determining means determines whether or not the temporarily held consumption degree exceeds a consumption limit higher than the consumption reference, the alarm notifying means output and notifies a predetermined replacement alarm when it is determined that the consumption degree exceeds the consumption limit, and the mechanical device also includes an operation control means for controlling the part using means to be inoperative when it is determined that the consumption degree exceeds the consumption limit.

4. A mechanical system at least comprising:

a chemical solution syringe including a cylinder member filled with a chemical solution and a piston member slidably inserted into the cylinder member; and a chemical solution injector for injecting the chemical solution into a patient by relatively moving the cylinder member and the piston member of the chemical solution syringe mounted removably;

further comprising a consumption storage means put on the chemical solution syringe for storing at least data of a consumption degree such that the consumption degree can be updated, wherein the chemical solution injector includes:

a piston driving mechanism for pressing the piston member into the cylinder member of the held chemical solution syringe;

a data reading means for reading the data of the consumption degree from the consumption storage means of the mounted chemical solution syringe;

a consumption holding means for temporarily holding the read data of the consumption degree;

a consumption detecting means for updating the temporarily held data of the consumption degree in accordance with operation of the piston driving mechanism;

a consumption determining means for determining whether or not the temporarily held consumption degree exceeds a predetermined consumption reference;

an alarm notifying means for outputting and notifying a predetermined replacement announcement when it is determined that the consumption degree exceeds the consumption reference; and a data writing means for writing the updated data of the consumption degree to the consumption storage means on the chemical solution syringe.

5. The mechanical system according to 4, wherein the consumption detecting means updates the data of the consumption degree in accordance with the number of uses of the chemical solution syringe.

6. The mechanical system according to 4, wherein the consumption detecting means updates the data of the consumption degree in accordance with the operating time of the chemical solution syringe.

7. The mechanical system according to 4, wherein the chemical solution injector also includes an output detecting means for detecting an operating output of the piston driving mechanism, and the consumption detecting means updates the data of the consumption degree in accordance with the operating time of the chemical solution syringe and the operating output of the piston driving mechanism.

8. A mechanical system at least comprising:

a chemical solution syringe including a cylinder member filled with a chemical solution and a piston member slidably inserted into the cylinder member;

a chemical solution injector for injecting the chemical solution into a patient by relatively moving the cylinder member and the piston member of the chemical solution syringe mounted removably; and a cylinder adapter for holding the cylinder member of the chemical solution syringe in the chemical solution injector;

further comprising a consumption storage means put on the cylinder adapter for storing at least data of a consumption degree such that the consumption degree can be updated, wherein the chemical solution injector includes:

a piston driving mechanism for pressing the piston member into the cylinder member held by the cylinder adapter;

a data reading means for reading the data of the consumption degree from the consumption storage means of the mounted cylinder adapter;

a consumption holding means for temporarily holding the read data of the consumption degree;

a consumption detecting means for updating the temporarily held data of the consumption degree in accordance with operation of the piston driving mechanism;

a consumption determining means for determining whether or not the temporarily held consumption degree exceeds a predetermined consumption reference;

an alarm notifying means for outputting and notifying a predetermined replacement announcement when it is determined that the consumption degree exceeds the consumption reference; and a data writing means for writing the updated data of the consumption degree to the consumption storage means on the cylinder adapter.

9. The mechanical system according to 8, wherein the consumption detecting means updates the data of the consumption degree in accordance with the number of uses of the cylinder adapter.

10. The mechanical system according to 8, wherein the consumption detecting means updates the data of the consumption degree in accordance with the operating time of the cylinder adapter.

11. The mechanical system according to 8, wherein the chemical solution injector also includes an output detecting means for detecting an operating output of the piston driving mechanism, and the consumption detecting means updates the data of the consumption degree in accordance with the operating time of the cylinder adapter and the operating output of the piston driving mechanism.

12. A mechanical system at least comprising:

a chemical solution syringe including a cylinder member filled with a chemical solution and a piston member slidably inserted into the cylinder member;

a chemical solution injector for injecting the chemical solution into a patient by relatively moving the cylinder member and the piston member of the chemical solution syringe mounted removably;

a secondary battery removably connected to the chemical solution injector to supply power thereto; and a battery-charging apparatus for receiving power from a commercial power source to charge the secondary battery removably connected thereto, further comprising a consumption storage means put on the secondary battery for storing at least data of a consumption degree such that the consumption degree can be updated, wherein the chemical solution injector includes:

a piston driving mechanism for pressing the piston member into the cylinder member by consuming power supplied from the secondary battery removably connected thereto;

a data reading means for reading the data of the consumption degree from the consumption storage means on the connected secondary battery;

a consumption holding means for temporarily holding the read data of the consumption degree;

a consumption detecting means for updating the temporarily held data of the consumption degree in accordance with operation of the piston driving mechanism;

a consumption determining means for determining whether or not the temporarily held consumption degree exceeds a predetermined consumption reference;

an alarm notifying means for outputting and notifying a predetermined replacement announcement when it is determined that the consumption degree exceeds the consumption reference; and a data writing means for writing the updated data of the consumption degree to the consumption storage means on the secondary battery.

13. The mechanical system according to 12, wherein the consumption detecting means updates the data of the consumption degree in accordance with the number of uses of the secondary battery.

14. The mechanical system according to 12, wherein the consumption detecting means updates the data of the consumption degree in accordance with the operating time of the secondary battery.

15. The mechanical system according to 12, wherein the chemical solution injector also includes an output detecting means for detecting the power consumed by the piston driving mechanism, and the consumption detecting means updates the data of the consumption degree in accordance with the operating time of the secondary battery and the power consumed by the piston driving mechanism.

16. The mechanical system according to any one of 8 to 15, wherein the chemical solution injector also includes an operation control means for controlling the piston driving mechanism to be inoperative when it is determined that the consumption degree exceeds the consumption reference.

17. The mechanical system according to any one of 8 to 15, wherein the consumption determining means determines whether or not the temporarily held consumption degree exceeds a consumption limit higher than the consumption reference, the alarm notifying means output and notifies a predetermined replacement alarm when it is determined that the consumption degree exceeds the consumption limit, and the chemical solution injector also includes an operation control means for controlling the piston driving mechanism to be inoperative when it is determined that the consumption degree exceeds the consumption limit.

18. A mechanical system at least comprising:

a secondary battery removably connected to a separate mechanical device to supply power thereto; and a battery-charging apparatus for receiving power from a commercial power source to charge the secondary battery removably connected thereto, further comprising a consumption storage means put on the secondary battery for storing at least data of the number of charges such that the data can be updated, wherein the battery-charging apparatus includes:

a battery-charging means for charging the connected secondary battery;

a data reading means for reading the data of the number of charges from the consumption storage means on the connected secondary battery;

a consumption holding means for temporarily holding the read data of the number of charges;

a consumption detecting means for updating the temporarily held data of the number of charges;

a consumption determining means for determining whether or not the temporarily held number of charges exceeds a predetermined consumption reference;

an alarm notifying means for outputting and notifying a predetermined replacement announcement when it is determined that the number of charges exceeds the consumption reference; and a data writing means for writing the updated data of the number of charges to the consumption storage means on the secondary battery.

19. A mechanical system at least comprising:

a secondary battery removably connected to a separate mechanical device to supply power thereto; and a battery-charging apparatus for receiving power from a commercial power source to charge the secondary battery removably connected thereto, further comprising a consumption storage means put on the secondary battery for storing at least data of a charge time such that the data can be updated, wherein the battery-charging apparatus includes:

a battery-charging means for charging the connected secondary battery;

a data reading means for reading the data of the charge time from the consumption storage means on the connected secondary battery;

a consumption holding means for temporarily holding the read data of the charge time;

a consumption detecting means for updating the temporarily held data of the charge time;

a consumption determining means for determining whether or not the temporarily held charge time exceeds a predetermined consumption reference;

an alarm notifying means for outputting and notifying a predetermined replacement announcement when it is determined that the charge time exceeds the consumption reference; and a data writing means for writing the updated data of the charge time to the consumption storage means on the secondary battery.

20. The mechanical system according to 18 or 19, wherein the consumption determining means determines whether or not the temporarily held consumption degree exceeds a consumption limit higher than the consumption reference, the alarm notifying means output and notifies a predetermined replacement alarm when it is determined that the consumption degree exceeds the consumption limit, and the chemical solution injector also includes an operation control means for controlling the battery-charging means to be inoperative when it is determined that the consumption degree exceeds the consumption limit.

21. The mechanical system according to any one of 1 to 20, wherein the consumption storage means is formed of an RFID (Radio Frequency Identification) chip, the data reading means is formed of an RFID reader, and the data writing means is formed of an RFID writer.

22. The mechanical device in the mechanical system according to 1, comprising:

a part using means for using and operating the consumable part removably mounted thereon;

a data reading means for reading the data of the consumption degree from the consumption storage means of the mounted consumable part;

a consumption holding means for temporarily holding the read data of the consumption degree;

a consumption detecting means for updating the temporarily held data of the consumption degree in accordance with operation of the part using means;

a consumption determining means for determining whether or not the temporarily held consumption degree exceeds a predetermined consumption reference;

an alarm notifying means for outputting and notifying a predetermined replacement announcement when it is determined that the consumption degree exceeds the consumption reference; and a data writing means for writing the updated data of the consumption degree to the consumption storage means on the consumable part.

23. The chemical solution injector in the mechanical system according to 4, comprising:

a piston driving mechanism for pressing the piston member into the cylinder member of the held chemical solution syringe;

a data reading means for reading the data of the consumption degree from the consumption storage means of the mounted chemical solution syringe;

a consumption holding means for temporarily holding the read data of the consumption degree;

a consumption detecting means for updating the temporarily held data of the consumption degree in accordance with operation of the piston driving mechanism;

a consumption determining means for determining whether or not the temporarily held consumption degree exceeds a predetermined consumption reference;

an alarm notifying means for outputting and notifying a predetermined replacement announcement when it is determined that the consumption degree exceeds the consumption reference; and a data writing means for writing the updated data of the consumption degree to the consumption storage means on the chemical solution syringe.

24. The chemical solution injector in the mechanical system according to 8, comprising:

a piston driving mechanism for pressing the piston member into the cylinder member held by the cylinder adapter;

a data reading means for reading the data of the consumption degree from the consumption storage means of the mounted cylinder adapter;

a consumption holding means for temporarily holding the read data of the consumption degree;

a consumption detecting means for updating the temporarily held data of the consumption degree in accordance with operation of the piston driving mechanism;

a consumption determining means for determining whether or not the temporarily held consumption degree exceeds a predetermined consumption reference;

an alarm notifying means for outputting and notifying a predetermined replacement announcement when it is determined that the consumption degree exceeds the consumption reference; and a data writing means for writing the updated data of the consumption degree to the consumption storage means on the cylinder adapter.

25. The chemical solution injector in the mechanical system according to 12, comprising:

a piston driving mechanism for pressing the piston member into the cylinder member by consuming power supplied from the secondary battery removably connected thereto;

a data reading means for reading the data of the consumption degree from the consumption storage means on the connected secondary battery;

a consumption holding means for temporarily holding the read data of the consumption degree;

a consumption detecting means for updating the temporarily held data of the consumption degree in accordance with operation of the piston driving mechanism;

a consumption determining means for determining whether or not the temporarily held consumption degree exceeds a predetermined consumption reference;

an alarm notifying means for outputting and notifying a predetermined replacement announcement when it is determined that the consumption degree exceeds the consumption reference; and a data writing means for writing the updated data of the consumption degree to the consumption storage means on the secondary battery.

26. The battery-charging apparatus in the mechanical system according to 18, comprising:

a battery-charging means for charging the connected secondary battery;

a data reading means for reading the data of the number of charges from the consumption storage means on the connected secondary battery;

a consumption holding means for temporarily holding the read data of the number of charges;

a consumption detecting means for updating the temporarily held data of the number of charges;

a consumption determining means for determining whether or not the temporarily held number of charges exceeds a predetermined consumption reference;

an alarm notifying means for outputting and notifying a predetermined replacement announcement when it is determined that the number of charges exceeds the consumption reference; and a data writing means for writing the updated data of the number of charges to the consumption storage means on the secondary battery.

27. The battery-charging apparatus in the mechanical system according to 19, comprising:

a battery-charging means for charging the connected secondary battery;

a data reading means for reading the data of the charge time from the consumption storage means on the connected secondary battery;

a consumption holding means for temporarily holding the read data of the charge time;

a consumption detecting means for updating the temporarily held data of the charge time;

a consumption determining means for determining whether or not the temporarily held charge time exceeds a predetermined consumption reference;

an alarm notifying means for outputting and notifying a predetermined replacement announcement when it is determined that the charge time exceeds the consumption reference; and a data writing means for writing the updated data of the charge time to the consumption storage means on the secondary battery.

28. The consumable part in the mechanical system according to 1, comprising a consumption storage means put on the consumable part for storing at least data of a consumption degree such that the consumption degree can be updated.

29. The chemical solution syringe in the mechanical system according to 4, comprising a consumption storage means put on the chemical solution syringe for storing at least data of a consumption degree such that the consumption degree can be updated.

30. The cylinder adapter in the mechanical system according to 8, comprising a consumption storage means put on the cylinder adapter for storing at least data of a consumption degree such that the consumption degree can be updated.

31. The secondary battery in the mechanical system according to any one of 12, 18, and 19, comprising a consumption storage means put on the secondary battery for storing at least data of a consumption degree such that the consumption degree can be updated.

What is claimed is:

1. A mechanical system at least comprising:
a chemical solution syringe including a cylinder member filled with a chemical solution, and a piston member slidably inserted into the cylinder member; and
a chemical solution injector for injecting the chemical solution into a patient by relatively moving the cylinder member and the piston member of the chemical solution syringe mounted removably;
further comprising a consumption storage means put on the chemical solution syringe for storing at least data of a consumption degree such that it can be updated,
wherein the chemical solution injector includes:
a piston driving mechanism for pressing the piston member into the cylinder member of the held chemical solution syringe;
data reading means for reading the data of the consumption degree from the consumption storage means on the mounted chemical solution syringe;
consumption holding means for temporarily holding the read data of the consumption degree;
consumption detecting means for updating the temporarily held data of the consumption degree;
consumption determining means for determining whether or not the temporarily held consumption degree exceeds a predetermined consumption reference;
alarm notifying means for outputting and notifying a predetermined replacement announcement when it is determined that the consumption degree exceeds the consumption reference; and
data writing means for writing the updated data of the consumption degree to the consumption storage means on the chemical solution syringe; and
wherein the consumption degree is an accumulation of the pressure of the piston member, and the consumption detecting means updates the data of the consumption degree in accordance with the pressure applied to the piston member by the piston driving mechanism.

2. The mechanical system according to claim 1, wherein the consumption detecting means updates the data of the consumption degree, in accordance with at least one of a number of uses and an operating time of the chemical solution syringe.

3. A mechanical system at least comprising:
a chemical solution syringe including a cylinder member filled with a chemical solution and a piston member slidably inserted into the cylinder member;
a chemical solution injector for injecting the chemical solution into a patient by relatively moving the cylinder member and the piston member of the chemical solution syringe mounted removably; and
a cylinder adapter for holding the cylinder member of the chemical solution syringe in the chemical solution injector;
further comprising a consumption storage means put on the cylinder adapter for storing at least data of a consumption degree such that it can be updated,
wherein the chemical solution injector includes:
a piston driving mechanism for pressing the piston member into the cylinder member held by the cylinder adapter;
data reading means for reading the data of the consumption degree from the consumption storage means of the mounted cylinder adapter;
consumption holding means for temporarily holding the read data of the consumption degree;
consumption detecting means for updating the temporarily held data of the consumption degree;
consumption determining means for determining whether or not the temporarily held consumption degree exceeds a predetermined consumption reference;
alarm notifying means for outputting and notifying a predetermined replacement announcement when it is determined that the consumption degree exceeds the consumption reference; and
data writing means for writing the updated data of the consumption degree to the consumption storage means on the cylinder adapter; and
wherein the consumption degree is an accumulation of the pressur of the piston member, and the consumption detecting means updates the data of the consumption degree in accordance with the pressure applied to the piston member by the piston driving mechanism.

4. The mechanical system according to claim 3, wherein the consumption detecting means updates the data of the consumption degree in accordance with at least one of a number of uses and an operating time of the cylinder adapter.

5. A mechanical system at least comprising:
a chemical solution syringe including a cylinder member filled with a chemical solution and a piston member slidably inserted into the cylinder member;
a chemical solution injector for injecting the chemical solution into a patient by relatively moving the cylinder member and the piston member of the chemical solution syringe mounted removably;
a secondary battery removably connected to the chemical solution injector to supply power thereto; and
a battery-charging apparatus for receiving power from a commercial power source and charging the secondary battery removably connected thereto,
further comprising a consumption storage means put on the secondary battery for storing at least data of a consumption degree such that it can be updated,
wherein the chemical solution injector includes:
piston driving mechanism for pressing the piston member into the cylinder member by consuming power supplied from the secondary battery removably connected thereto;
data reading means for reading the data of the consumption degree from the consumption storage means on the connected secondary battery;
consumption holding means for temporarily holding the read data of the consumption degree;
consumption detecting means for updating the temporarily held data of the consumption degree;
consumption determining means for determining whether or not the temporarily held consumption degree exceeds a predetermined consumption reference;

alarm notifying means for outputting and notifying a predetermined replacement announcement when it is determined that the consumption degree exceeds the consumption reference; and data writing means for writing the updated data of the consumption degree to the consumption storage means on the secondary battery; and wherein the chemical solution injector also includes an output detecting means for detecting the power consumed by the piston driving mechanism, and the consumption detecting means updates the data of the consumption degree in accordance with (i) an operating time of the secondary battery and (ii) the power consumed by the piston driving mechanism.

6. The mechanical system according to claim 5, wherein the consumption detecting means updates the data of the consumption degree, in accordance with at least one of a number of uses and an operating time of the secondary battery.

7. The mechanical system according to claim 1, wherein the chemical solution injector also includes an operation control means for controlling the piston driving mechanism to be inoperative when it is determined that the consumption degree exceeds the consumption reference.

8. The mechanical system according to claim 7, wherein the consumption determining means determines whether or not the temporarily held consumption degree exceeds a consumption limit higher than the consumption reference, the alarm notifying means output and notifies a predetermined replacement alarm when it is determined that the consumption degree exceeds the consumption limit, and the chemical solution injector also includes an operation control means for controlling the piston driving mechanism to be inoperative when it is determined that the consumption degree exceeds the consumption limit.

9. The mechanical system according to claim 1, wherein the consumption storage means is a RFID (Radio Frequency Identification) chip, the data reading means is a RFID reader, and the data writing means is a RFID writer.

* * * * *